US00PP37016P2

(12) United States Plant Patent
Moon

(10) Patent No.: US PP37,016 P2
(45) Date of Patent: Oct. 14, 2025

(54) ***QUERCUS* TREE NAMED 'QPMTF3'**

(50) Latin Name: *Quercus phellos*
Varietal Denomination: QPMTF3

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 19/083,825

(22) Filed: Mar. 19, 2025

(51) Int. Cl.
*A01H 5/00* (2018.01)
*A01H 6/00* (2018.01)

(52) U.S. Cl.
USPC ..... Plt./225
CPC ..... *A01H 6/00* (2018.05)

(58) Field of Classification Search
USPC ..... Plt./225
CPC ..... A01H 5/00
See application file for complete search history.

*Primary Examiner* — Kent L Bell

(57) ABSTRACT

A new and distinct cultivar of *Quercus phellos* tree named 'QPMTF3' is disclosed, characterized by a distinctive pyramidal shape with branches occurring at acute angles through the canopy. Leaves emerge bright green and turn dark green. Foliage is held on the tree long into Fall. The new variety is a *Quercus* tree, typically used for landscapes and gardens.

2 Drawing Sheets

Figure 1:
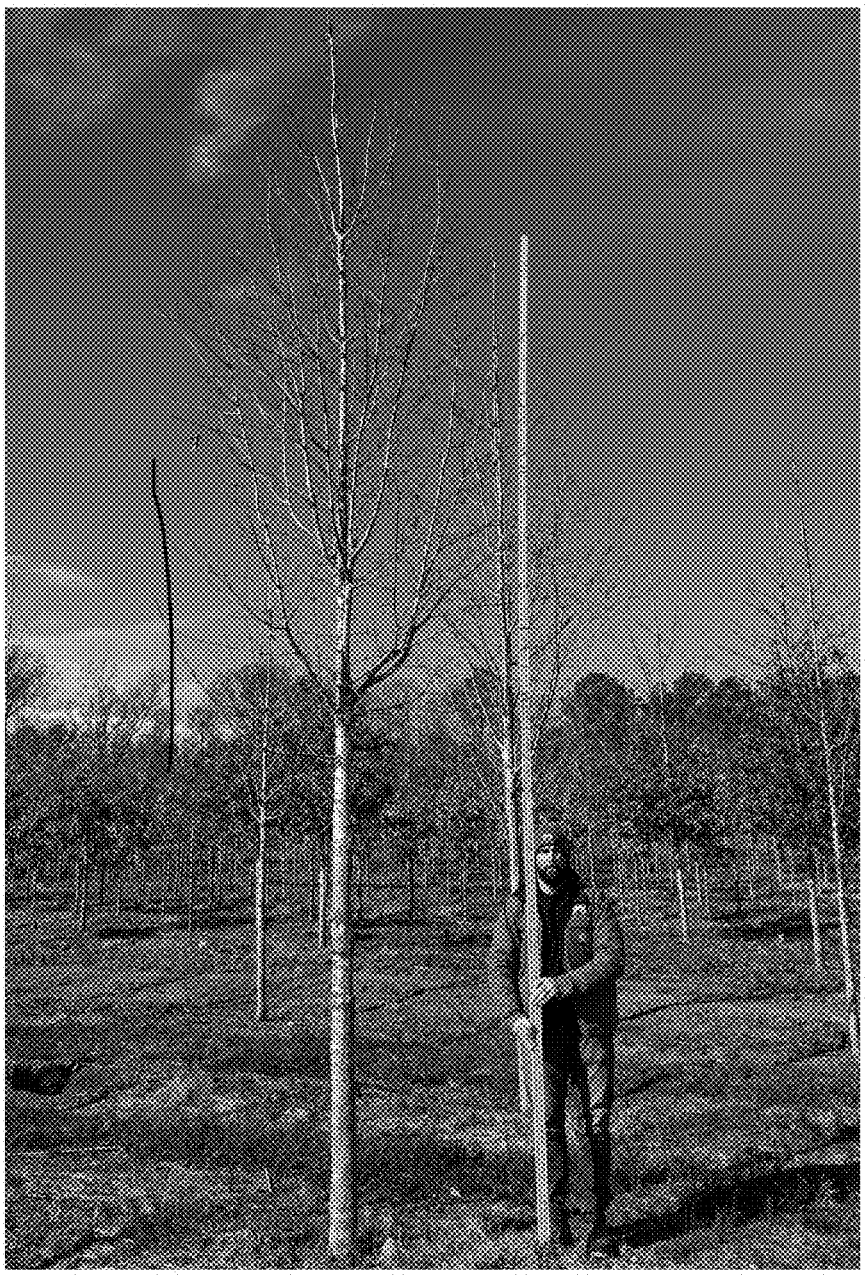

Latin name of the genus and species: *Quercus phellos.*
Variety denomination: 'QPMTF3'.

BACKGROUND OF THE INVENTION

The new cultivar is a product of a planned breeding program. The new variety was discovered growing as a seedling among a group of open-pollinated *Quercus phellos* trees at a tree farm in Washington, Georgia. A single seedling tree was observed which had a distinctive pyramidal shape with branches occuring at acute angles through the canopy than the other seedlings among this group. The inventor made this discovery in the Summer of 2020. The exact seed and pollen parents cannot be identified. The open-pollination resulting in the new variety took place during 2016.

Asexual reproduction by grafting of the new cultivar 'QPMTF3' was first performed during summer of 2021 at a farm in Washington, Georgia. The cleft grafting system developed by the inventor has resulted in progeny that have proven the characteristics of the new variety to be genetically stable. This grafting process involved taking cuttings in February, being grafted, and being placed in calloused chambers for approximately three weeks. They are then moved into 3"×6" tree band pots and placed in humidity chambers for approximately four weeks. Furthermore, these observations have confirmed that the new variety represents a new and improved variety of *Quercus phellos* tree as particularly evidenced by the larger leaves, darker more dense canopy, holds foliage longer, dark green mature leaves against new bright green leaves, and dominant central leader. These genetic traits can be consistently reproduced by asexual propagation.

SUMMARY OF THE INVENTION

The cultivar 'QPMTF3' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'QPMTF3' grown in Washington, Georgia. These characteristics in combination distinguish 'QPMTF3' as a new and distinct *Quercus phellos* cultivar:

1. Upright and up-swept branches.
2. Tight pyramidal shape, which is unique for *Quercus phellos.*
3. Fast growth rate; approximately ¼ inch of caliper growth per year in the first 4 years.
4. Narrow canopy at a young age
5. Dominant central leader.
6. Large leaves.

PARENT COMPARISON

The parent varieties cannot be specifically identified.

COMMERCIAL COMPARISON

Plants of the new cultivar 'QPMTF3' are similar to plants of *Quercus phellos* 'QPSTJ', U.S. Plant Pat. No. 19,922, in most horticultural characteristics, however, plants of the new cultivar 'QPMTF3' differ in the following:

1. Branches of the new variety occur at more acute angles than this comparator, making a narrower canopy.
2. The new variety holds its leaves longer into Fall than this comparator.
3. The new variety does not grow as fast as this comparator, forming a medium sized rather than large tree.

Plants of the new cultivar 'QPMTF3' are similar to plants of *Quercus phellos* 'QPSTA', U.S. Plant Pat. No. 13,677, in most horticultural characteristics, however, plants of the new cultivar 'QPMTF3' differ in the following:

1. Branches of the new variety occur at more acute angles than this comparator, making a narrower canopy.
2. The new variety holds its leaves longer into Fall than this comparator.
3. The new variety does not grow as fast as this comparator, forming a medium sized rather than large tree.

Plants of the new cultivar 'QPMTF3' are similar to plants of *Quercus phellos* 'QPSTB', U.S. Plant Pat. No. 18,321, in most horticultural characteristics, however, plants of the new cultivar 'QPMTF3' differ in the following:

1. Branches of the new variety occur at more acute angles than this comparator, making a narrower canopy.
2. The new variety holds its leaves longer into Fall than this comparator.
3. The new variety has yellow Fall foliage; this comparator has red Fall foliage.

Plants of the new cultivar 'QPMTF3' are similar to plants of *Quercus phellos* 'RT3', U.S. Plant Pat. No. 16,444, in most horticultural characteristics, however, plants of the new cultivar 'QPMTF3' differ in the following:

1. The new variety has foliage which is about 40% longer than foliage of this comparator.
2. The new variety holds its leaves longer into Fall than this comparator.

Plants of the new cultivar 'QPMTF3' are similar to plants of *Quercus phellos* 'QPMTF', U.S. Plant Pat. No. 15,217, in most horticultural characteristics, however, plants of the new cultivar 'QPMTF3' differ in the following:

1. Foliage of the new variety is larger by about 40% to 50% than this comparator.
2. Foliage of the new variety is darker green than foliage of this comparator.

BRIEF DESCRIPTION OF THE PHOTOGRAPHS

The accompanying photograph in FIG. 1 illustrates a tree of the new variety at about 3 years of age planted in a field. The photograph was taken during winter while the tree has no foliage, allowing the branch structure to be clearly seen.

Figure 2:
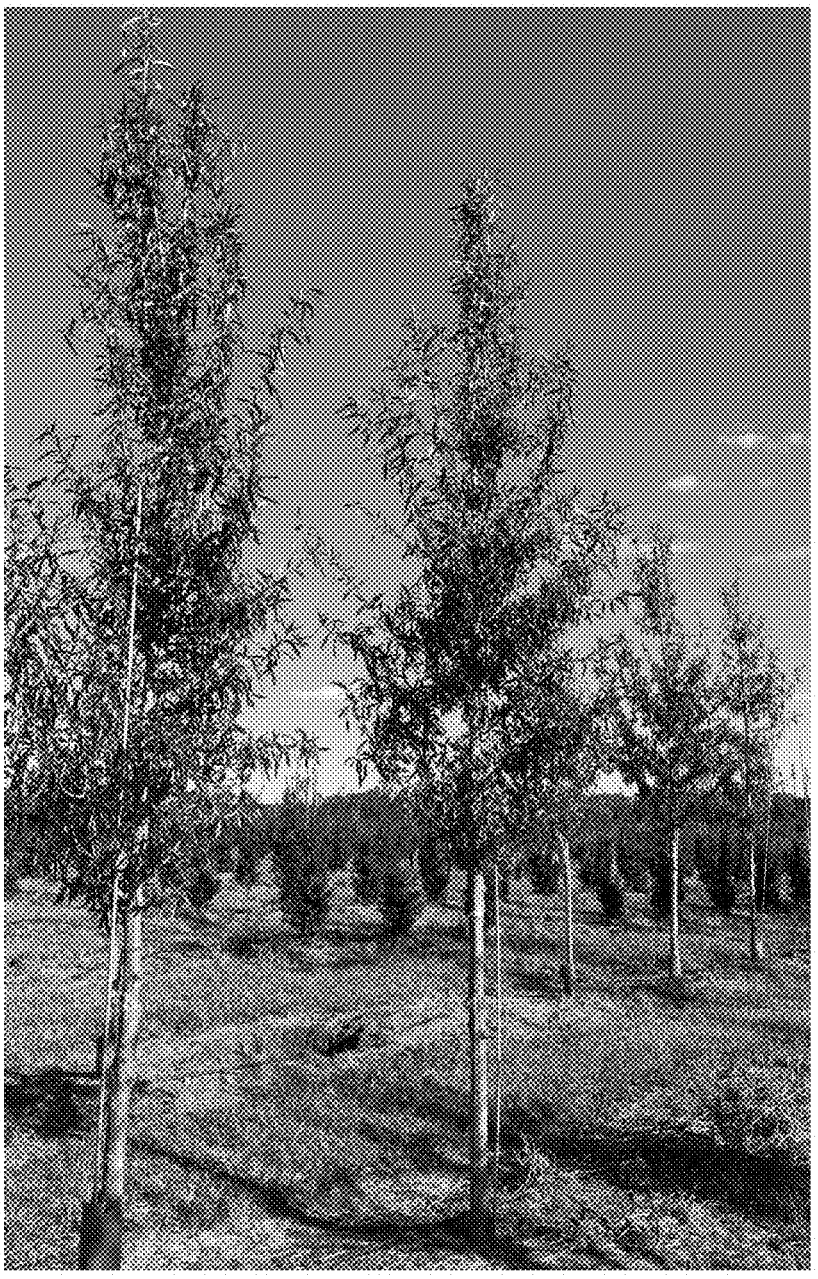

FIG. 2 illustrates multiple 2-year old trees of the new variety during June in Washington, GA. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'QPMTF3' plants grown outdoors at a nursery in Washington, Georgia. Plants described are approximately 2 years old, unless otherwise noted. Temperatures ranged from 5° C. to 10° C. at night to 18° C. to 27° C. during the day. Measurements and numerical values represent averages of typical plant types.

Botanical classification: *Quercus phellos* 'QPMTF3'.

PROPAGATION

Cleft grafting.

Root Description: Woody, somewhat fibrous. Moderately dense. N200A.

TREE

Growth Habit: Deciduous pyramidal tree.

Height: Approximately 14 feet at 3 years.

Spread: Approximately 4 feet at 3 years.

Branch/Stem color:

*New Growth*.—Near RHS. Yellow-Green 146C.

*Mature*.—Near RHS Greyed-Green 197A, streaks near Grey-Brown 199A. Texture: Moderately dense lenticels on both new and mature growth. 2 mm long, 1 mm. Mature growth scaly.

Aspect and Angle: Lower 1/3 of branches at 30 to 45 degrees from center. Upper 2/3 of branches 30 degrees or less from center.

Trunk Characteristics:

*Diameter*.—About 2.5 inches measured at approximately 3 inches above soil level at 3 years.

*Color*.—Near RHS Greyed-Green 198D, mottled 198A with blotches Black 202B and Greyed-Green 197A.

*Surface Texture*.—Moderately scaly.

FOLIAGE

Leaf:

*Arrangement*.—Alternate.

*Shape*.—Elliptic.

*Average Length*.—Average 11.5 cm to 14 cm excluding petiole.

*Average Width*.—Approximately 2 cm.

*Apex*.—Acute.

*Base*.—Tapered.

*Margin*.—Entire.

*Texture of top surface*.—Glabrous.

*Texture of lower surface*.—Glabrous.

*Color*.—Young foliage: Upper side: Near RHS Green 143A. Under side: Near RHS Green 143B. Mature foliage: Upper side: Near RHS Green 137A. Under side: Near RHS Green 137D. Fall foliage: Upper side: Near RHS Yellow 11A mottled Green 137A. Under side: Near RHS Yellow 11A and 10C mottled Green 137D.

*Venation*.—Type: Pinnate. Color: Venation color upper side: Near RHS Yellow-Green 144D. Venation color under side: Near RHS Yellow-Green 145C.

*Petiole*.—Length: Average range 1 cm to 1.8 cm. Diameter: Average 2 mm. Color: Upper side: Near RHS Yellow-Green 144D. Under side: Near RHS Yellow-Green 145C.

FLOWER

Not observed to date.

REPRODUCTIVE ORGANS

Not observed to date.

OTHER CHARACTERISTICS

Disease/Pest resistance: Neither resistance nor susceptibility to normal diseases and pests of *Quercus* has been observed.

Drought Tolerance: No tolerance for drought observed. *Quercus phellos* can be moderately drought tolerant once established.

Temperature tolerance: USDA Zones 6 through 9.

Fruits/Nuts: Not observed.

What is claimed is:

1. A new and distinct cultivar of *Quercus phellos* tree named 'QPMTF3' as herein illustrated and described.

* * * * *